(12) United States Patent  
Schembri et al.

(10) Patent No.: US 7,880,108 B2
(45) Date of Patent: Feb. 1, 2011

(54) DEFLECTION PLATE

(75) Inventors: Frank Schembri, San Mateo, CA (US); David Vrane, San Jose, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 515 days.

(21) Appl. No.: 11/978,060

(22) Filed: Oct. 26, 2007

(65) Prior Publication Data

US 2009/0107893 A1 Apr. 30, 2009

(51) Int. Cl.
*B03C 7/00* (2006.01)
(52) U.S. Cl. .................. 209/128; 209/129; 209/130
(58) Field of Classification Search .......... 209/128–130
See application file for complete search history.

(56) References Cited

U.S. PATENT DOCUMENTS

| 670,440 | A | * | 3/1901 | Sutton et al. ................ 209/130 |
| 1,297,159 | A | * | 3/1919 | Hedberg .................... 209/130 |
| 2,479,615 | A | * | 8/1949 | Guizzetti ................... 209/181 |
| 3,079,318 | A | * | 2/1963 | Milan ....................... 204/518 |
| 3,755,128 | A | * | 8/1973 | Herwig .................... 204/228.3 |
| 3,826,364 | A |   | 7/1974 | Bonner et al. |
| 3,923,624 | A | * | 12/1975 | Beekmans et al. ....... 422/82.03 |
| 3,988,233 | A | * | 10/1976 | Gamer et al. .............. 204/415 |
| 3,989,613 | A | * | 11/1976 | Gritzner .................... 204/543 |
| 4,349,367 | A | * | 9/1982 | Krumwiede ................. 65/27 |
| 4,667,830 | A |   | 5/1987 | Nozaki, Jr. et al. |
| 5,411,644 | A | * | 5/1995 | Neukermans ............... 205/765 |
| 5,483,469 | A |   | 1/1996 | Van den Engh et al. |
| 5,700,692 | A |   | 12/1997 | Sweet |
| 6,116,184 | A | * | 9/2000 | Solayappan et al. ........ 118/50.1 |
| 6,170,668 | B1 | * | 1/2001 | Babko-Malyi ........... 209/127.1 |
| 6,372,506 | B1 |   | 4/2002 | Norton |
| 6,809,804 | B1 |   | 10/2004 | Yount et al. |
| 6,880,414 | B2 |   | 4/2005 | Norton |
| 7,201,875 | B2 |   | 4/2007 | Norton et al. |

* cited by examiner

*Primary Examiner*—Joseph C Rodriguez
(74) *Attorney, Agent, or Firm*—Douglas A. Petry (57) ABSTRACT

The present invention provides deflection plates for use in a flow-type particle sorter that are resistant to wetting. The deflection plates include a gas-porous, conductive plate. A gas, such as air, is passed through the plate from the outer face (away from the particle flow) towards the inner face (towards the particle flow). The flow of gas prevents condensation on the inner face of the defection plate.

16 Claims, 9 Drawing Sheets

DEFLECTION PLATE

BACKGROUND OF THE INVENTION

1. Field of the Invention

The present invention relates to the field of particle sorters and, in particular, to particle sorting by flow cytometry.

2. Description of Related Art

Flow-type particle sorting systems, such as sorting flow cytometers, are used to sort particles in a fluid sample based on at least one measured characteristic of the particles. In a flow-type particle sorting system, particles, such as molecules, analyte-bound beads, or individual cells, in a fluid suspension are passed in a stream by a detection region in which particle sensing means senses particles contained in the stream of the type to be sorted. The fluid suspension is jetted from a nozzle and vibrated to break the stream into uniform discrete drops. The signal, or signals, from the particle sensing means are processed to provide a signal output when a particle of the type to be sorted is sensed that triggers assorting mechanism to separate the drop containing the particle from the stream of drops. A number of methods of sorting particles are known in the art, including the use of moving droplet capture tubes (as described in U.S. Pat. No. 5,030,002) and electrostatic sorting. In electrostatic sorting, drop charging means are connected to the stream to charge drops containing a particle of the type to be sorted with an electrical charge as it breaks off from the jet stream. The stream of drops is passed through a transverse electrostatic field established by a pair of oppositely charged deflection plates. Uncharged drops are not deflected passing through the electrostatic field and are collected by a central receptacle. Charged drops containing a particle of the type to be sorted are deflected in a direction and amount related to the polarity and magnitude of the drop charge and are collected in a separate collection receptacle.

Particle sensing typically is carried out by passing the fluid stream by a detection region in which the particles are exposed to an excitation light, typically from one or more lasers, and the light scattering and fluorescence properties of the particles are measured. Particles or components thereof can be labeled with fluorescent dyes to facilitate detection, and a multiplicity of different particles or components may be simultaneously detected by using spectrally distinct fluorescent dyes to label the different particles or components. Typically, detection is carried out using a multiplicity of photodetectors to facilitate the independent measurement of the fluorescence of each distinct dye.

The transverse electrostatic field typically is established by a pair of oppositely charged deflection plates flanking the drop stream. The deflection plates are connected to opposite-polarity dc potential sources of, for example, from ±1000 to ±5000 volts. Positively charged drops passing between the deflection plates are deflected towards the negatively charge deflection plate, and negatively charged drops are deflected towards the positively charged deflection plate. The position and lengths of the deflection plates are such that deflected drops do not collide with a plate, but are deflected sufficiently to be collected by a separate collection receptacle held below plates.

Sorting flow cytometers similar to the type described above are described, for example, in U.S. Pat. Nos. 3,826,364; 4,667,830; 5,483,469; 5,700,692; 6,372,506; 6,809,804; 6,880,414; and 7,201,875; the entire contents of each patent being incorporated by reference herein. Flow sorters are described in "Flow Sorters for Biological Cells" by Tore Lindmo, Donald C. Peters, and Richard G. Sweet, Flow Cytometry and Sorting, 2d ed. (New York: Wiley-Liss, Inc., 1990), pages 145-169, and in Shapiro, 2003, Practical Flow Cytometry (John Wiley and Sons, Inc. Hoboken, N.J.), both incorporated herein by reference. Commercially available sorting flow cytometers include the BD FACSVantage™ and BD FACSAria™ sorting flow cytometers manufactured by BD Biosciences (San Jose, Calif.).

One problem that arises in the use of flow-type particle sorters results from the undesired formation during droplet formation of aerosols that can remain suspended in the air in the sort chamber. The aerosol particles can settle on the deflection plates, causing wetting of the deflection plates. Because of the high voltages applied to the plates, wetting of the plates can result in arcing and loss of deflection plate charge, thus interfering with the correct functioning of the sorter.

BRIEF SUMMARY OF THE INVENTION

The present invention provides deflection plates for use in a flow-type electrostatic particle sorter, such as a flow cytometer, that are resistant to wetting. The deflection plates of the present invention are made of a porous conductive material. In a preferred embodiment, the deflection plates of the present invention comprise a metal plate made using a sintering process.

The porous deflection plate is held in the sorter such that one face ("the inside face") of the deflection plate is in contact with the interior of the sort chamber, facing the sample stream, and the opposite face of the defector plate ("the outside face") is in contact with the exterior of the sort chamber. During operation, a pressure difference is maintained between the interior of the sort chamber in contact with inside face of the deflection plate and the exterior of the sort chamber in contact with the outside face of the deflection plate, such that air flows through the porous deflection plate into the sort chamber. The difference in pressure can be maintained either by providing pressurized air to the outside face of the deflection plate, or by reducing the air pressure in the sort chamber. The flow of air through the deflection plate inhibits the formation of fluid droplets on the plate, and rapidly eliminates any droplets that do form.

In some embodiments, the porous deflection plate is held in a holder that forms a plenum behind the plate and includes an air inlet into the plenum from a source outside the sort chamber. The plenum is fully enclosed but for the air inlet and the porous deflection plate, such that air that exits the plenum through the porous deflection plate is replenished through the air inlet. In some embodiments, pressurized air is provided through the air inlet into the plenum to maintain the pressure inside the plenum higher than the pressure in the sort chamber. In other embodiments, the air inlet is open to the air outside the sort chamber, and the pressure inside the sort chamber is maintain at a lower pressure using an aspirator. In either case, air flows into the plenum through the air inlet and exits through the deflection plate into the sort chamber.

In some embodiments, the porous deflection plate is held in the wall of, and forms part of the wall of, an enclosed sort chamber, such that the inside face of the deflection plate is in contact with the interior of the sort chamber, and the outside face of the deflection plate is in contact with the exterior of the sort chamber. Air is evacuated from the sort chamber by an aspirator, and the evacuated air is replaced by air flowing through the porous deflection plate into the sort chamber.

In one aspect, the present invention provides a deflection plate apparatus for use in a flow-type electrostatic particle sorter that comprises a porous deflection plate, a plate holder that holds the plate and forms a plenum behind the plate, and an air inlet for providing air into the interior of the plenum. The deflection plate apparatus may additionally contain an electrode connected to the deflection plate for providing an electrical charge to the deflection plate.

In another aspect, the present invention provides a sort chamber for use in a flow-type sorter, wherein the sort chamber comprises porous deflection plates positioned in the wall of the sort chamber such that the deflection plates form part of the wall of the sort chamber. Air is evacuated from the sort chamber by an aspirator, and the evacuated air replaced by air flowing into the sort chamber through the porous deflection plate.

In another aspect, the present invention provides a flow-type electrostatic particle sorter, such as a flow cytometer, containing at least one porous deflection plate of the present invention.

In another aspect, the present invention provides a flow-type electrostatic particle sorter, such as a flow cytometer, containing at least one deflection plate apparatus of the present invention.

In another aspect, the present invention provides a flow cytometer containing an enclosed sort chamber comprising porous deflection plates, wherein the porous deflection plates are positions such that inside face of each deflection plate is exposed to the interior of the sort chamber, and the outside face of the deflection plate is in contact with the exterior of the sort chamber. Thus, the present invention proves a flow-type electrostatic particle sorter comprising:

a) an enclosed sort chamber;
b) a flow cell mounted on top of the sort chamber capable of providing a stream of droplets into the interior of the sort chamber and of selectively charging droplets;
c) a plurality of collection vessels, positioned to receive droplets from the sample stream in the interior of the sort chamber;
d) a plurality of gas-permeable deflection plates disposed to deflect charged droplets in the stream of droplets, each plate having an inside face and an outside face, wherein the inside face is in the interior of the sort chamber, positioned towards the stream of droplets, and wherein the outside face is connected to the outside of the sort chamber; and
e) an aspirator connected to the sort chamber for evacuating gas from the interior of the sort chamber, wherein the aspirator reduces pressure within the sort chamber such that a gas enters the chamber from outside the container through the gas-permeable deflection plates.

In some embodiments of the flow-type electrostatic particle sorter having an enclosed sort chamber, each of the gas-permeable deflection plates is held in a holder that forms a plenum whose interior includes the outside face of the deflection plate, wherein the holder comprises an air inlet connecting the plenum with the outside of the sort chamber, such that the gas that enters the chamber from outside the container through the gas-permeable deflection plates passes through the air inlet into the plenum and exits through the gas-permeable deflection plate.

In other embodiments of the flow-type electrostatic particle sorter having an enclosed sort chamber, each of the gas-permeable deflection plates is mounted in a wall of the sort chamber such that the deflection plates form part of the wall of the sort chamber, wherein the inner face of the deflection plate is exposed to the interior of the sort chamber, and the outer face of the gas-permeable deflection plate is in contact with the exterior of the sort chamber.

DETAILED DESCRIPTION OF THE INVENTION

As used herein, "sort chamber" refers to the area in which electrostatic sorting takes place. By necessity, the term must include both physically defined chambers and more open configurations having only a partial, or even no, enclosure. Typically, a particle sorter includes an enclosed or partially enclosed area surrounding the deflection plates, between which the sample stream travels. This area may be defined by a physical enclosure used to confine the sorted material and protect against contamination, or simply by the nearest wall of the instrument, itself. However, sorting can be carried out using a minimum of structure, wherein the sample stream travels through an open area flanked by the deflection plates. The term sort chamber is used herein to refer the area in which sorting takes place, regardless of the extent of physical structures delimiting this area.

As used herein, an "enclosed sort chamber" refers to a sort chamber that is enclosed by walls such that the movement of gas into and out of the chamber is controllable. In the present invention, the movement of gas out of an enclosed sort chamber will be through an outlet connected to an aspirator, and the movement of gas into the enclosed sort chamber will be gas-permeable deflection plates of the present invention.

Figure 1:
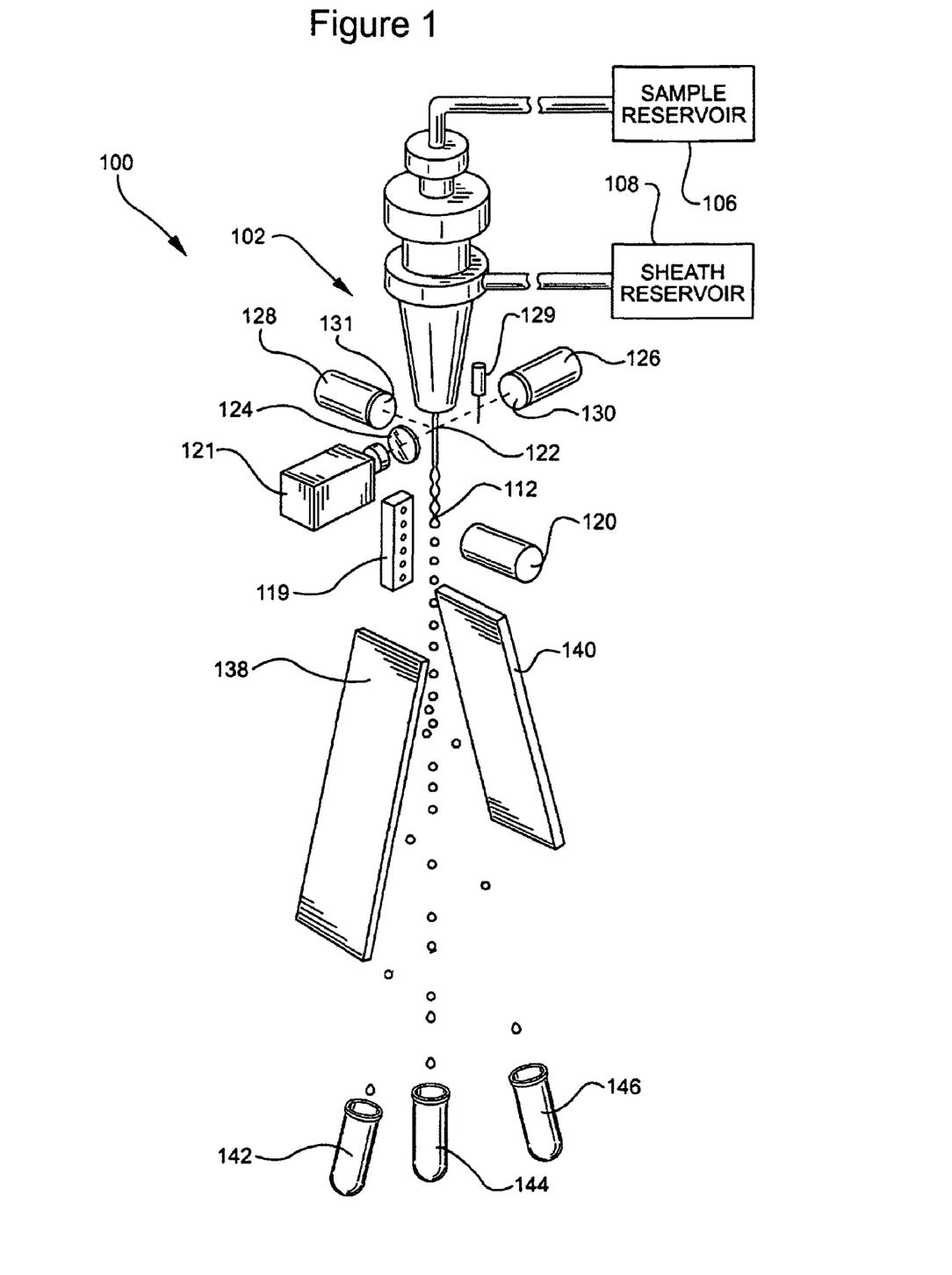
FIG. 1 is a schematic perspective view of a flow cytometer employing an apparatus according to an embodiment of the present invention.
Figure 2:
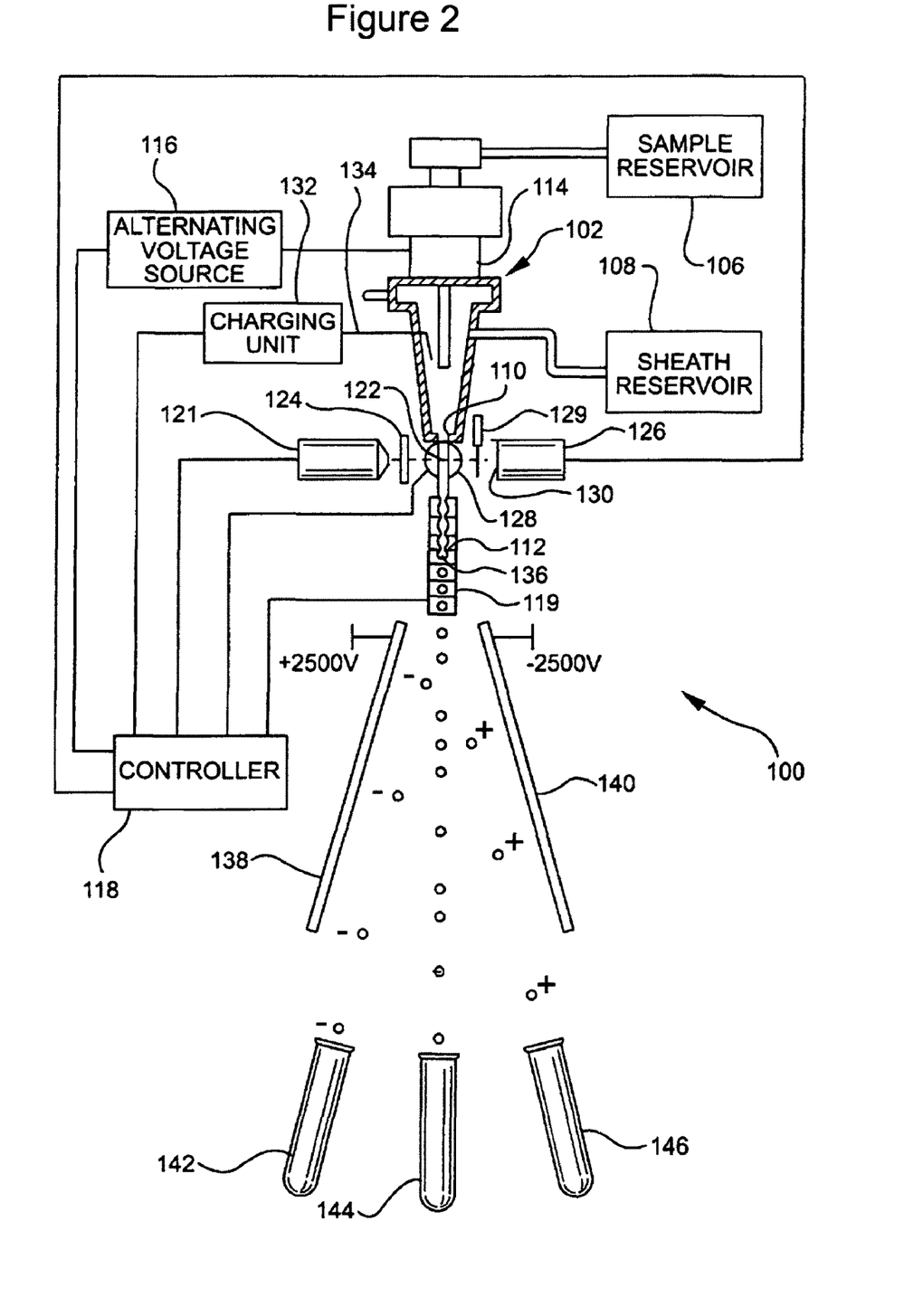
FIG. 2 is a schematic illustration of a front view of a portion of the flow cytometer shown in FIG. 1.

FIGS. 1 and 2 depict elements of a sorting flow cytometer 100 employing electrostatic particle sorting. Flow cytometer 100 includes a flow cell 102. The flow cytometer further includes a sample reservoir 106 for holding a fluid sample containing the particles to be sorted, and a sheath reservoir 108 containing a sheath fluid. The flow cytometer transports both the sample fluid and the sheath fluid to the flow cell 102. Within the flow cell 102, the sheath fluid surrounds the sample fluid, and the combined sheath fluid and sample fluid exit the flow cell 102 via an opening 110 as a sample stream ("flow stream" or "particle stream"). The flow cell 102 is designed such that the particle-containing sample fluid is hydrodynamically focused into the center of the flow stream, surrounded by particle-free sheath fluid.

Excitation light from laser 121 is focused by lens 124 onto the flow stream at detection region 122 (also known as the observation region or interrogation point). As illustrated, the detection region is below the flow cell opening at a point where the sample stream is intact. Flow cytometers in which the detection point is outside the flow cell are referred to as stream-in-air cytometers. Alternatively, a flow cell having an optically transmissive portion at the bottom, such as a cuvette with a fluid channel, can be used, with the detection region located in the fluid channel. A sorting flow cytometer utilizing a cuvette is described in U.S. Pat. No. 7,201,875, incorporated herein by reference.

An oscillating device 114 is provided to impart oscillations in the pressure of the sample stream. As depicted, the oscillation device is attached to the body of the flow cell and vibrates the entire flow cell. Alternatively, the oscillator can be connected to a nozzle at opening 110 or adapted to impart oscillations directly to the fluid. A sorting flow cytometer having an oscillator that imparts oscillations directly to the fluid, without vibrating the flow cell or nozzle, is described in U.S. Pat. No. 7,201,875, incorporated herein by reference. The oscillator, typically a piezoelectric element, is connected to an alternating voltage source 116 whose output voltage amplitude, frequency and phase is controlled by a controller 118.

The sample stream remains intact for some distance after exiting opening 110, until breaking off into droplets at the droplet break-off point 112. The oscillations of the sample stream pressure resulting from the oscillations of oscillation device 114 causes the sample stream to break-off into individual droplets 136 at the droplet break-off point 112. The distance from opening 110 at which the droplet break-off point 112 occurs, and the frequency or rate at which the droplets are formed, are governed by the fluid pressure and by the amplitude and frequency of oscillation of oscillating device 114, which are controlled by controller 118.

To view the droplet break-off point 112, a light source 119, such as an LED array, can be positioned in the region of the sample stream containing the droplet break-off point 112. The controller 118 can control the light source 119 to strobe at a desired frequency, so that a detector 120, such as a camera or other optical viewing device, can be used to view the region of the sample fluid stream containing the droplet break-off point 112.

The flow cytometer 100 further includes photodetectors 126 and 128, which can be, for example, photomultiplier tubes (PMTs), avalanche photo diodes, photodiodes, or any other suitable light-detecting device. Detector 126 is positioned to detect excitation light that is scattered by particles at a low angle relative to the excitation beam, referred to as forward scatter light. Obscuration bar 129 is positioned directly in the excitation beam path to block unscattered excitation light from entering detector 126. Detector 128 is positioned to detect excitation light that is scattered by particles at nearly right angles to the excitation beam, referred to as side scatter light.

Detectors 126 and 128 can also detect fluorescent light emitted from particles in the sample stream. Filters 130 and 131 can be positioned in front of the light receiving areas of detectors 126 and 128, respectively, to select the range of wavelength detected. Although detectors 126 and 128 are shown as individual detectors for exemplary purposes, typically a plurality of detectors are used together with wavelength demultiplexing optics, such as a series of dichroic-mirrors, adapted such that each detector detects a different range of wavelengths. Typically, fluorescent light is detected using detector 128, which is at right angles to the excitation beam, to minimize interference from the direct excitation light.

Detectors 126 and 128 each convert the light they receive into electrical signals which are interpreted by controller 118 as representing a characteristic of a particle passing the detection region 122 at a give sampling time. Particles are identified based on the characteristics measured.

In electrostatic sorting, the flow stream is electrically charged at the moment when a droplet containing a particle of interest is being formed, thus producing a charged droplet containing the particle of interest. The controller 118 controls charging unit 132, which includes an output electrode 134 that contacts the mixture of sample fluid and sheath fluid in flow cell 102. Following detection of a particle of interest (i.e., a particle to be sorted) in the detection region 122, controller 118 controls the charging unit 132 to charge the sample stream at a delayed time corresponding to the time when the particle has traveled from the detection region 122 to the droplet break-off region 112 and is present in a droplet breaking off from the sample fluid stream. The resulting droplet 136, which contains the particle of interest, retains the charge applied to the sample stream at the time of droplet break-off.

The charged droplet 136 continues descending from break-off point 112, passing between deflection plates 138 and 140, to which are applied opposite polarity DC potentials, such as +2,500 V and −2,500 V, respectively. Depending on the polarity of charge applied to droplet 136, the droplet 136 will either be attracted to deflection plate 138 and repelled by deflection plate 140, or vice-versa. Assuming, for example, that a negative potential has been applied to deflection plate 140 and a positive potential has been applied to deflection plate 138, if a positive charge has been applied to droplet 136, droplet 136 will be attracted to deflection plate 140 and repelled by deflection plate 138. Conversely, if a negative charge has been applied to droplet 136, droplet 136 will be attracted to deflection plate 138 and repelled by deflection plate 140.

As further illustrated, the flow cytometer 100 includes a plurality of collection vessels 142, 144, and 146. Droplets that have been negatively charged will be directed by the potentials applied to the deflection plates 138 and 140 toward collection vessel 142. Droplets 136 that have been neither positively nor negatively charged will not be deflected by the potentials applied to deflection plates 138 and 140, and continue along their original path into central collection vessel 144. Droplets 136 that have been positively charged will be deflected by the potentials applied to deflection plates 138 and 140 toward collection vessel 146.

As shown in FIGS. 1 and 2, particles are sorted into one of two collection vessels based on the polarity of the charge applied at the time of droplet break-off, or are left uncharged and collected in a central vessel. The degree of deflection from the central path can be controlled by the magnitude of the droplet charge, and particles can be sorted into one of four or more collection vessels (two on each side of the central collection vessel the collects uncharged particles) based both on the polarity and the magnitude of the charge applied at the time of droplet break-off.

The controller 118 must accurately control the timing of the sample stream charging to account for the drop delay time, which is the time between when a particle of interest passes through the detection region and when the same particle is incorporated into a droplet, in order to obtain a charged particle containing the particle of interest. Techniques for measuring and adjusting the drop delay are described in, for example, U.S. Pat. Nos. 5,700,692 and 6,372,506, each incorporated herein by reference.

Porous Deflection Plates

Porous deflection plates of the present invention consist of, or comprises, a gas-porous plate of a conductive material. The gas-porous, conductive plate preferably consists of a metal plate made by a sintering process, which process is well known in the art. Alternatively, the metal plate can be manufactured with an array of small holes of a size suitable to allow the passage of gas through the plate.

The porous, conductive deflection plates of the present invention will be of a length and width suitable for use in a flow-type particle sorter. The deflection plates of the present invention exhibit electrical properties essentially identical to those exhibited by the solid metal deflection plates well known in the art. The deflection plate dimensions and position relative to the flow stream suitable for use in a flow-type particle sorter suitable for use in a given application will be selected routinely following the teaching in the art applicable to solid metal deflection plates.

As used herein, the surface of the deflection plate that faces the sample stream is referred to as the "inside face", and the opposite surface of the deflection plate, which faces away from the sample stream, is referred to as the "outside face".

Most applications of particle sorting, including cell sorting, are carried out in an air environment. However, it is anticipated that some application may require sorting particles in some other gaseous environment, such as in an inert gas. For convenience, the invention is described herein primarily using air flow through the porous deflection plates to inhibit the formation of fluid droplets on the plate. However, it will be clear that any suitable gas can be used with the porous deflection plates of the present invention.

Figure 3:
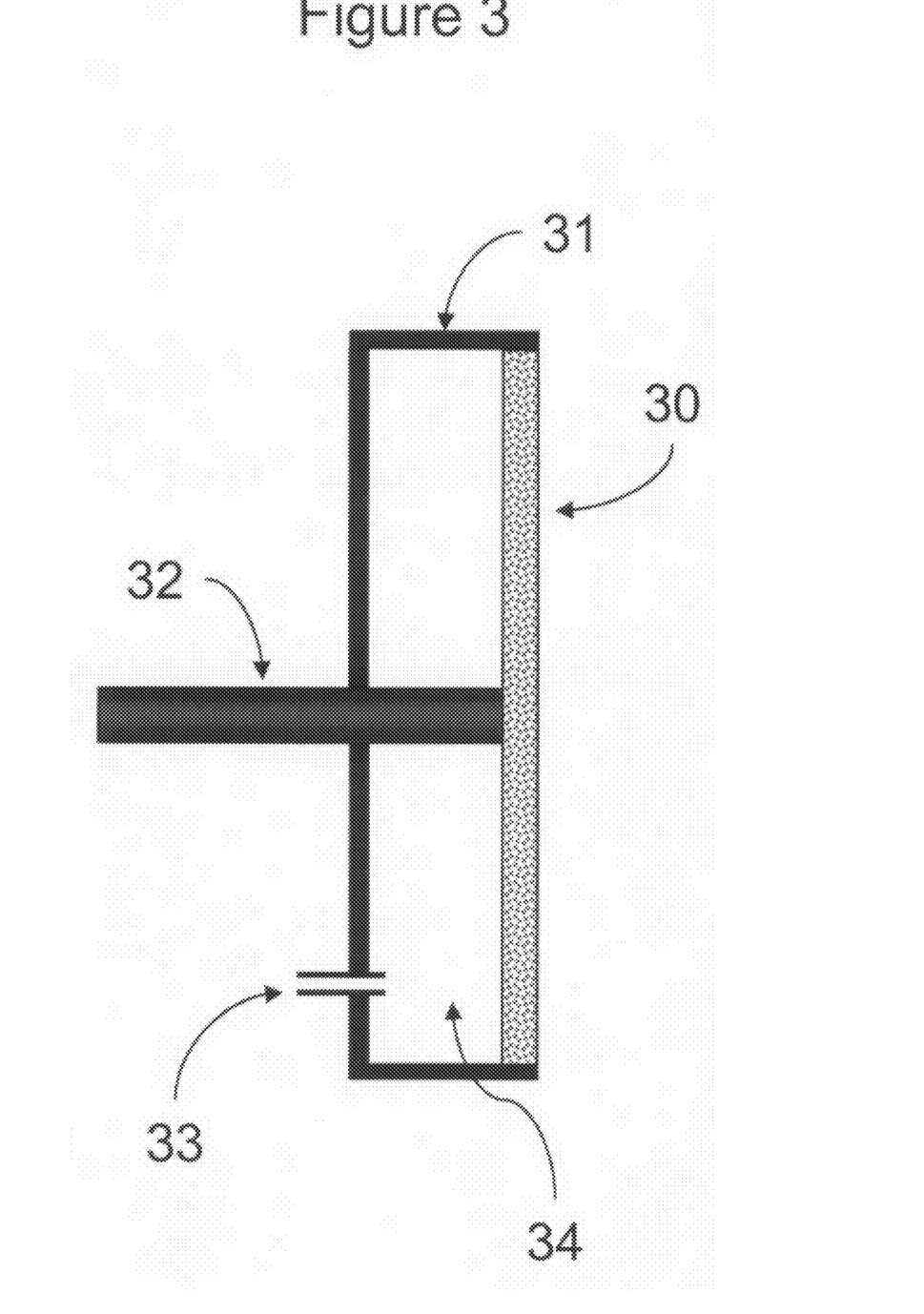
FIG. 3 shows a side view of an embodiment of the deflection plate apparatus of the present invention.
Figure 4:
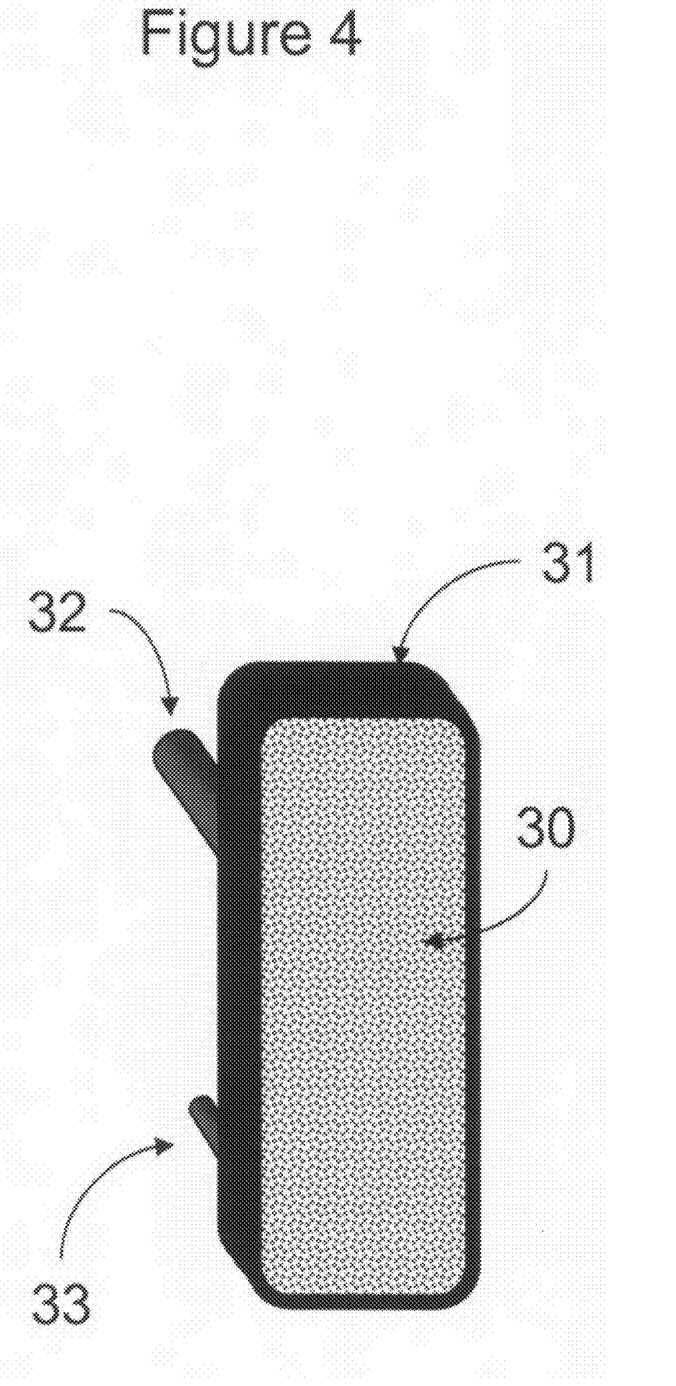
FIG. 4 shows a front-angled view of the deflection plate apparatus shown in FIG. 3.

Deflection Plate Apparatus (FIGS. 3-4)

FIGS. 3 and 4 depict a side view and a front-angle view, respectively, of an embodiment of the deflection plate apparatus of the present invention. Porous deflection plate 30 is held in holder 31, which forms a plenum 34 behind deflection plate 30. Electrode 32 provides an electrical connection to the deflection plate 30, and is used to charge the plate with an electrical potential. Air inlet 33 can be attached to a positive-pressure air supply to provide pressurized air into plenum 34. Air inlet 33 preferably is terminated externally in a connector, such as a barb-style connector, that facilitates easy connection to an air supply tube (not shown).

Holder 31 preferably is made from a non-conductive material, such as plastic, and serves to hold deflection plate 30 and create plenum 34. Alternatively, holder 31 can be made from a conductive material, in which case electrode 32 need only be in contact with holder 31 to enable charging of deflection plate 30, or some combination of non-conductive and conductive materials. The electrode (charging post) 32 also can serve as a structural member, used to hold the deflection plate apparatus in position. In another embodiment, electrode 32 can comprise a channel that serves as the air inlet 33 (e.g., a hollow metal tube), which eliminates the need for a separate air inlet.

In practice, the deflection plate apparatus is positioned in the sort chamber of the particle sorter such that the deflection plate is facing the sample stream. Air inlet 33 is used to provide air (or other gas) to the inside of plenum 34 at a pressure greater than the pressure inside the flow cell, along the inner face of the deflection plate. In some embodiments, the sort chamber is maintained at atmospheric pressure and pressurized air is fed into the plenum through the air inlet. In other embodiments, the sort chamber is maintained at reduced pressure and air at atmospheric pressure is allowed to enter through the air inlet. In either case, the pressure gradient across the deflection plate will cause air to flow out through the porous metal deflection plate 31 into the sort chamber. The flow of air through the deflection plate will decrease the formation of water droplets on the deflection plate, and lead to rapid evaporation of any water droplets that do form on the deflection plate.

Figure 5:
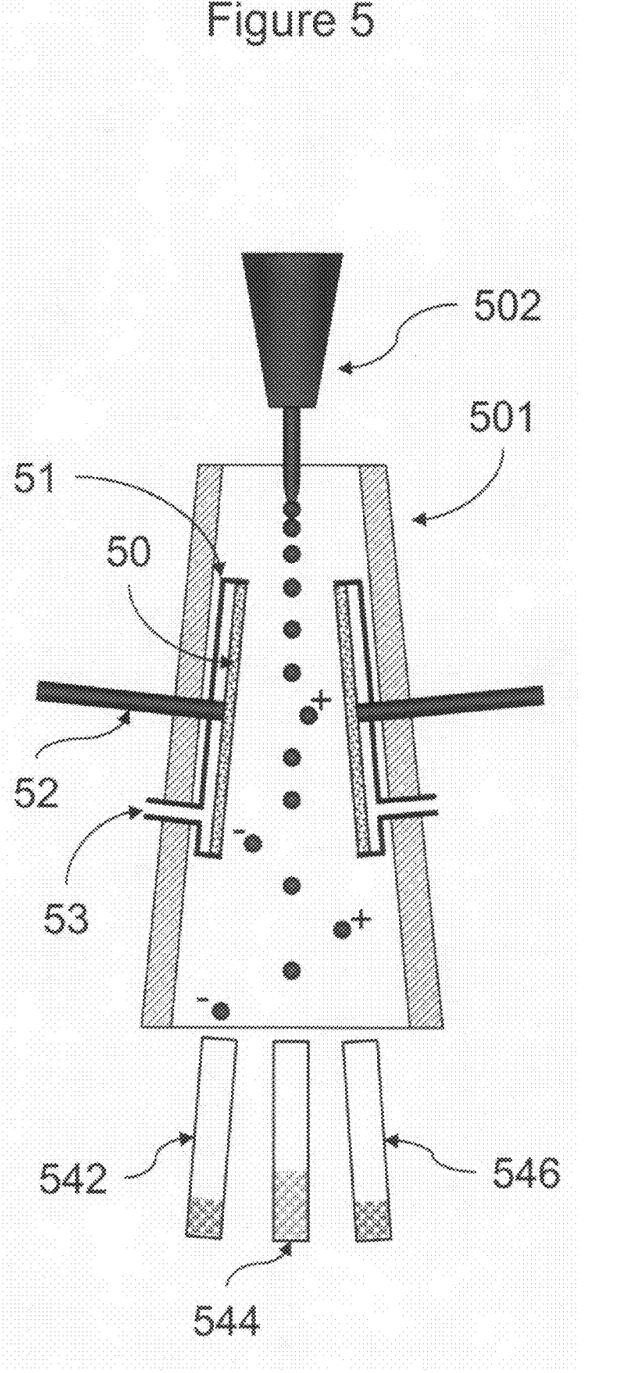
FIG. 5 shows a front, inside view of an embodiment of the sort chamber of the present invention comprising deflection plate apparatus positioned inside the sort chamber, vented to the outside of the sort chamber through an air inlet.

Open Sort Chamber (FIG. 5)

FIG. 5 depicts a front view of an embodiment of the invention in which sorting is carried out within sort chamber 501 that is open to the atmosphere at the top and bottom. Flow cell 502 is position such that the sample stream is injected into the interior of the chamber 501 through the top opening. Deflection plate apparatus, including deflection plate 50 mounted in holder 51 and in contact with electrode 52, are held inside the sort chamber. Electrode 52 is connected to a power supply for providing an electrical charge to the deflection plate.

A plurality of collection vessels, 542, 544, and 546, are positioned to collect negatively charged droplets, uncharged droplets, and positively charged droplets, respectively (assuming that deflection plate to the left of the sample stream is positively charged and the corresponding deflection plate to the right of the sample stream is negatively charged).

Air inlet 53 is connected to a pressurized air source to provide a positive pressure within plenum formed by holder 51 and deflection plate 50, thus increasing the pressure of the outer face of the deflection plate (inside the plenum) relative to the inner face of the defection plate (facing the sample stream). The increased pressure inside the plenum will cause air to flow out through the porous metal deflection plate 50.

Although sort chamber 501 is depicted as being defined by walls flanking the sample stream path and deflection plates, it will be clear that this physical structure is not necessary. It is sufficient for the deflection plates to be held in positions flanking the droplet stream.

Figure 6:
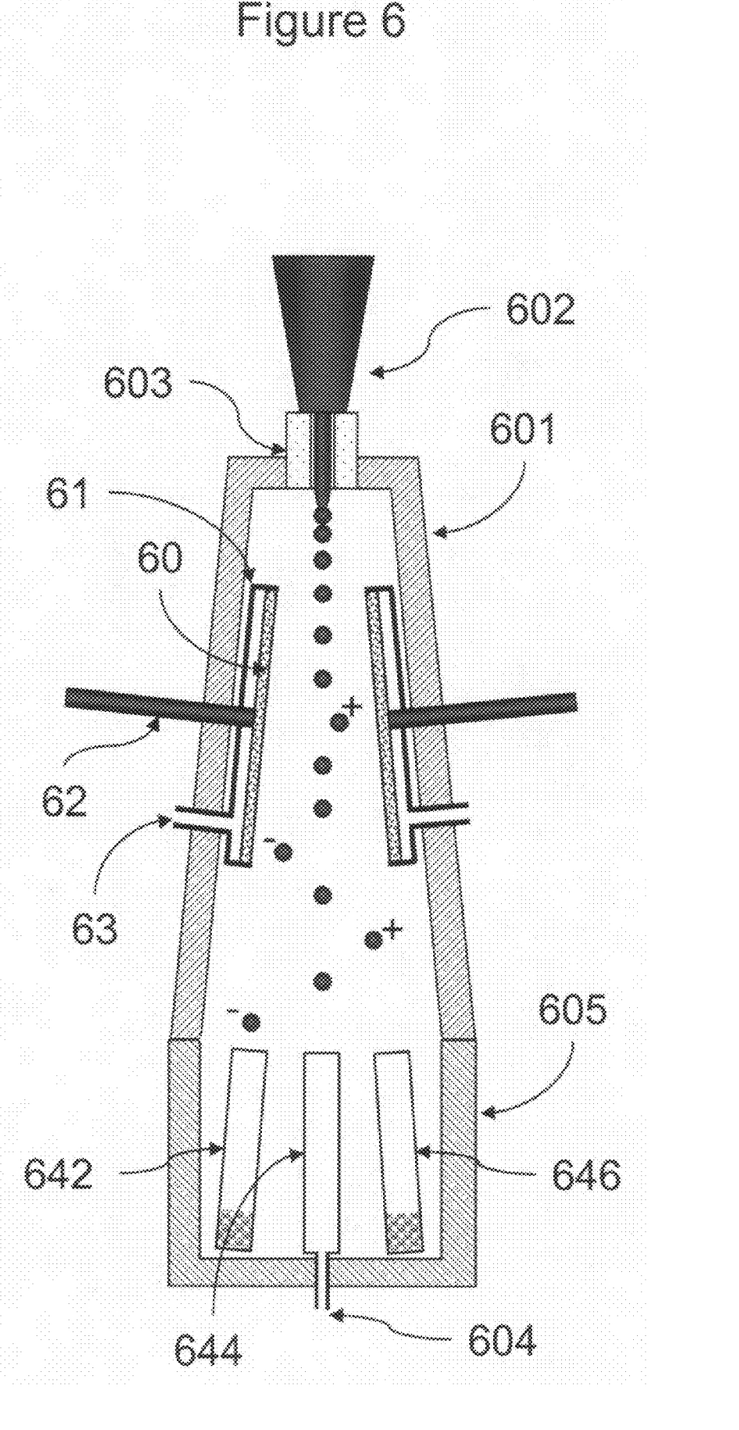
FIG. 6 shows a front, inside view of an embodiment of the sealed sort chamber of the present invention comprising deflection plate apparatus positioned inside the sort chamber, vented to the outside of the sort chamber through the air inlet, wherein the sort chamber is sealed.
Figure 7:
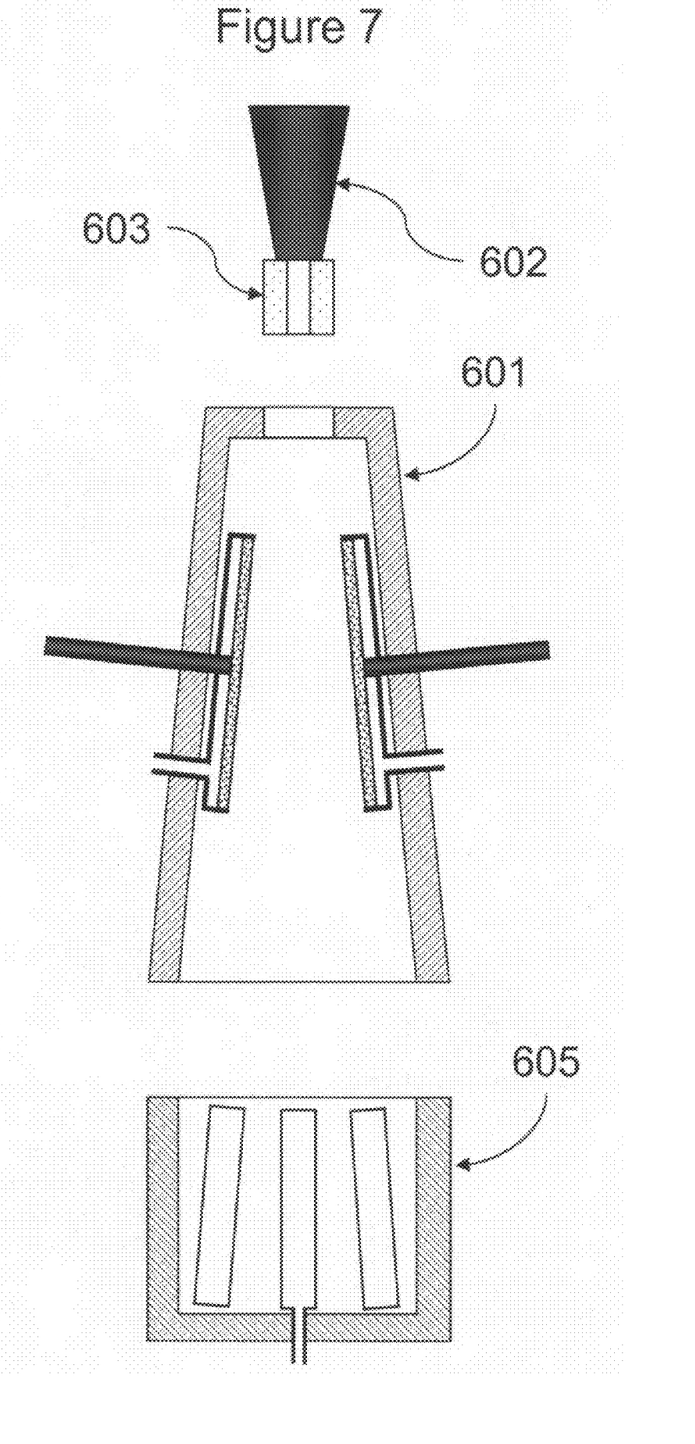
FIG. 7 shows an exploded view of the sort chamber shown in FIG. 6.

Enclosed Sort Chamber (FIGS. 6-7)

FIG. 6 depicts a front, inside view of an embodiment of the invention in which sorting is carried out within a fully enclosed sort chamber. FIG. 6 shows the interior of chamber 601; the front wall of the chamber is not shown. Flow cell 602 includes cuvette 603 made of a substantially clear material, such as clear plastic or any other suitable material, having a flow channel through it. Flow cell 602 is mounted at the top of chamber 601 such that there is essentially no leakage of air between the flow cell and the top of chamber 601, and such that the sample stream is injected into the interior of the chamber 601. The sample detection region is located in the cuvette above chamber 601. Alternatively, the sample detection region can be located inside chamber 601, in which chamber 601 will include transparent windows in the walls to enable illumination of the detection region with an external excitation light and collection of emission light from the detection region.

A collection container 605 holding a multiplicity of collection vessels, 642, 644, and 645, is mounted at the bottom of chamber 601 such that there is essentially no leakage of air between the collection container 605 and the chamber 601. Collection vessel 644 includes an outlet 604, which is connected to a vacuum source to aspirate unsorted (uncharged) particles and air, thus reducing the pressure inside chamber 601.

Deflection plate apparatus, including deflection plate 60 mounted in holder 61 and in contact with electrode 62, are positioned inside chamber 601. Electrode 62 is connected to a power supply for providing an electrical charge to the deflection plate. Air inlet 63 is vented to the outside of the sealed chamber 601 to provide air at atmospheric pressure into the plenum formed by deflection plate 60 and holder 61. Air aspirated from the interior of chamber 601 through outlet 604 is replaced by air flowing into the plenum through inlet 63 and out through porous metal deflection plate 60.

FIG. 7 depicts an exploded front view of the embodiment of the invention shown in FIG. 6, wherein the flow cell 602 and the collection container 605 are separated from chamber 601.

The sort chamber of the present invention can include additional elements. In the embodiment depicted in FIGS. 6 and 7, the sealed sort chamber is assembled from multiple components (chamber 601, flow cell 602, and collection container 605), similar to the sealed sort chamber described in U.S. Pat. No. 6,880,414, incorporated herein by reference, describes a sealed sort chamber having a multipurpose device for the aspiration of aerosols, the collection of unsorted particles, and the interruption of the sort in case of error, which may be useful in the present invention in place of outlet 604. In the sealed sort chamber described in U.S. Pat. No. 6,880, 414, air aspirated from the sealed sort chamber is replaced by air flowing into the sort chamber through small air passages in the sort block, whereas in the present invention, air aspirated from the sealed sort chamber is replaced by air flowing into the sort chamber through the porous deflection plates of the present invention. Other elements described in U.S. Pat. No. 6,880,414, that may be used with the present invention include a sort block (analogous to chamber 601) having a block body and a block face with an O-ring present along the edge of the face to ensure a tight seal of the block face to the block body.

Embodiments of the present invention in which sorting is carried out in sealed sort chamber are particularly useful for applications that require the complete isolation of the sample from the outside environment, including the instrument operator, such as in sorting hazardous materials or in applications which require that contamination of the sample be avoided, such as sterile cell sorting. All aerosols can be contained within the sealed chamber and evacuated through an outlet (e.g., outlet 604), as the positive air flow through the deflection plates into the chamber prevents the escape of any aerosols. The entire sort chamber can be sterilized as before use and/or replaced as an intact unit, which minimizes the chance of contamination of any components outside of the chamber or of contamination of the sample from previous sorts.

Figure 8:
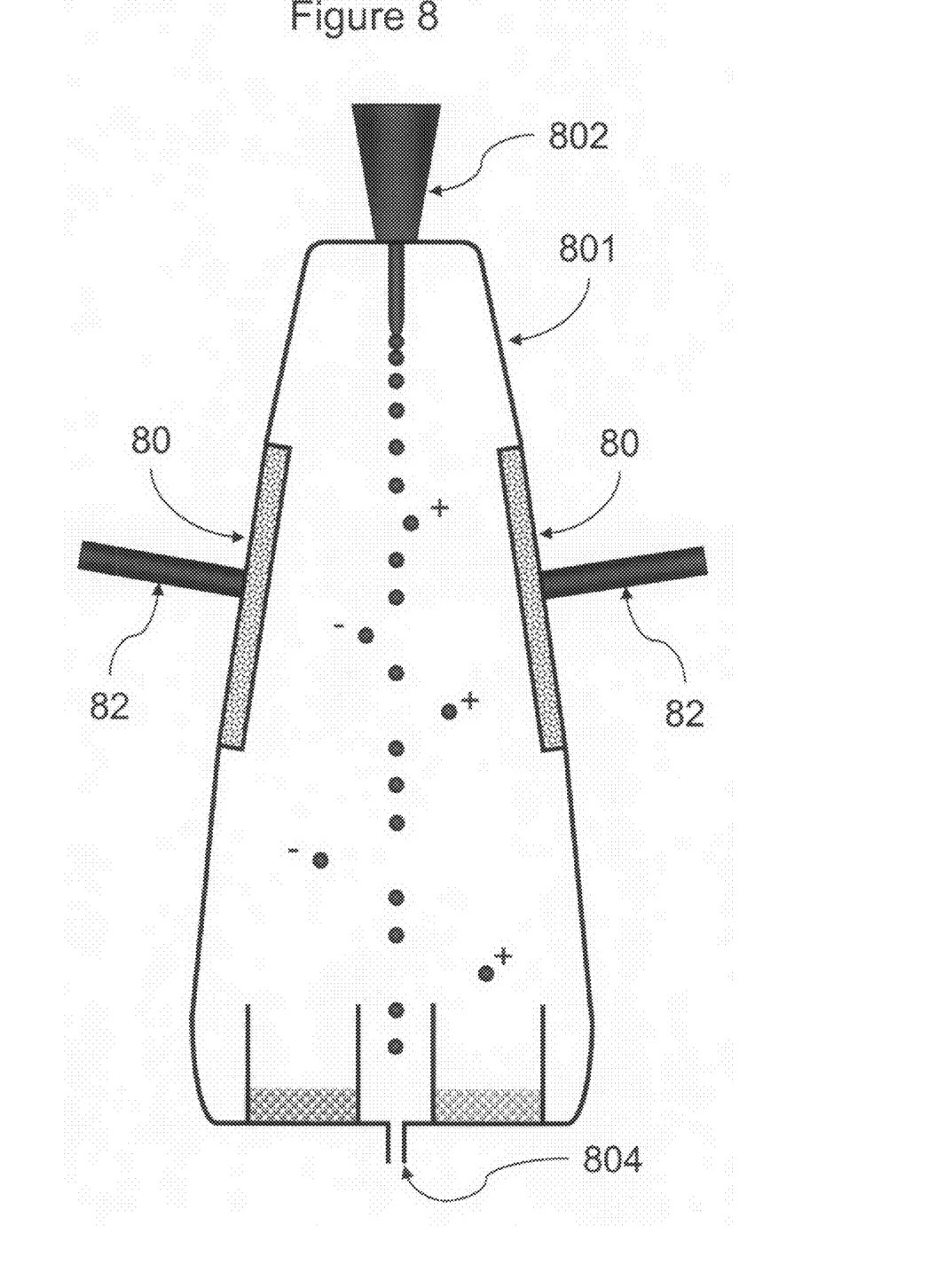
FIG. 8 shows a front, inside view of an embodiment of a sealed sort chamber of the present invention comprising porous deflection plates positioned in the wall of the sort chamber.
Figure 9:
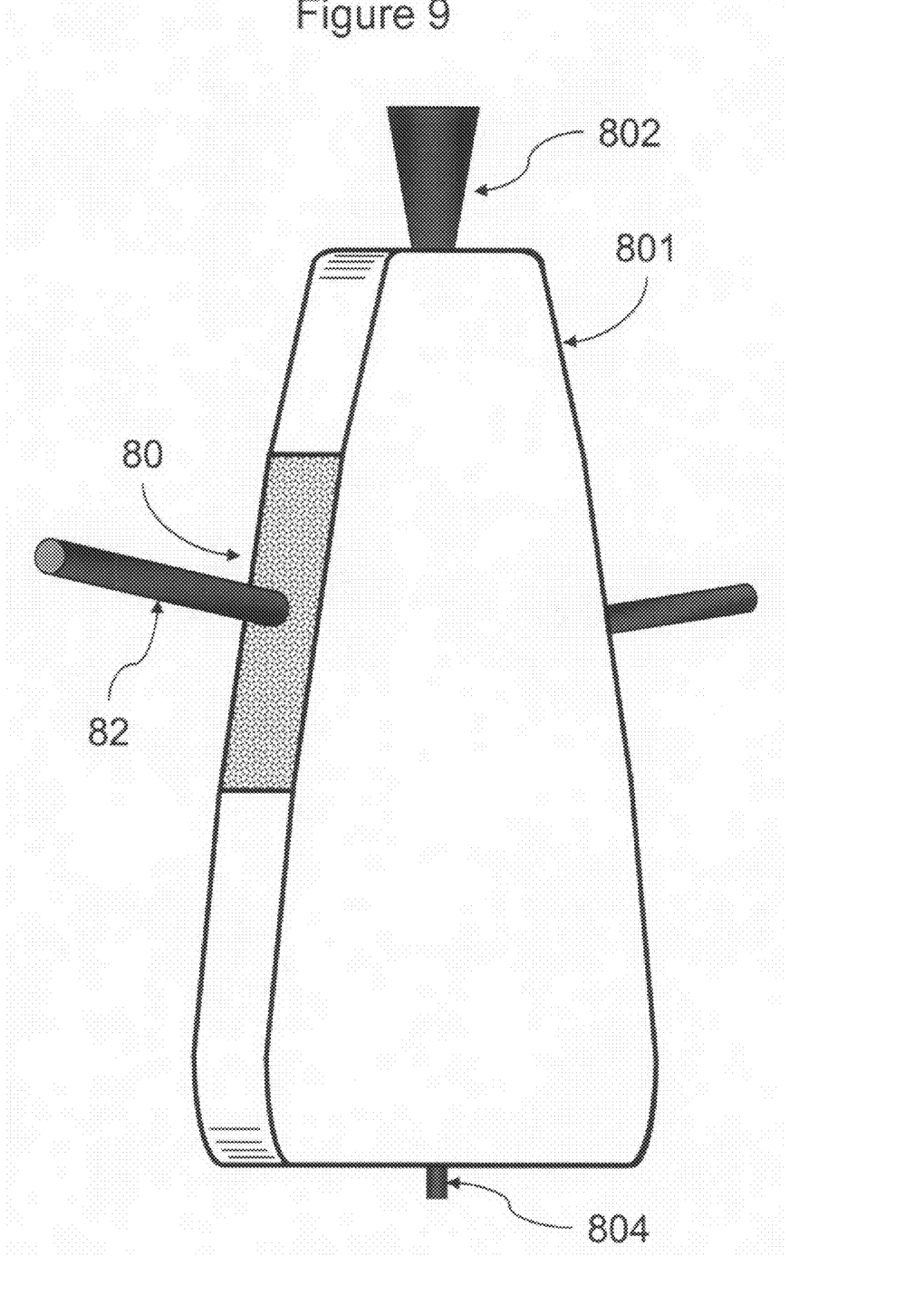
FIG. 9 shows a front-angled view of the sealed sort chamber shown in FIG. 8.

Enclosed Sort Chamber (FIGS. 8-9)

FIG. 8 depicts a front, inside view of an embodiment of the invention in which sorting is carried out within a fully enclosed chamber 801. FIG. 8 shows the interior of chamber 801; the front wall of the chamber is not shown. In this embodiment, porous deflection plates 80 are mounted in, and form part of, the wall of chamber 801, with the inner face of each the deflection plate forming part of the inner wall of the chamber, and the outer face of the deflection plate exposed to the atmosphere outside the chamber. Thus, the porous deflection plates provide a path for air to flow into chamber 801, and air aspirated from the interior of chamber 801 through outlet 804 is replaced by air flowing into the chamber through the porous deflection plates.

As shown in FIG. 8, flow cell 802 injects the flow stream directly into the interior of chamber 801, and the sample detection region is located inside chamber 801. In this embodiment, chamber 801 will include transparent windows in the walls to enable illumination of the detection region with an external excitation light and collection of emission light from the detection region. Alternatively, a flow cell with a cuvette can be used such that the detection region is located above chamber 801, similar to that shown in FIG. 6.

FIG. 9 shows a front-angle view of the fully enclosed sorting chamber shown in FIG. 8. In this view, the sorting chamber 801 is shown with the front cover in place. Deflection plate 80 is shown forming part of the side wall of chamber 801, with the outer face exposed to the surrounding atmosphere.

The incorporation of the porous deflection plates directly into the walls of the chamber reduces the number of parts comprising the sort chamber and potentially provides savings in the manufacturing costs. This is particularly suited for applications in which the entire sort chamber is disposed after each sort to minimized the chance of contamination. The entire chamber, including the deflection plates, can be sterilized before use, and replaced after sorting a sample. Preferably, the chamber can be joined to the flow cell using a simple press-fit joint such that replacement of the chamber does not affect the positioning of the flow cell.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the claims.

We claim:

1. An deflection plate apparatus for use in a flow-type electrostatic particle sorter comprising:
   a gas-permeable deflection plate made entirely from a conductive material,
   a holder that holds the gas-permeable plate such that a plenum is formed behind the gas-permeable plate, wherein said holder comprises an air inlet into said plenum, and wherein said plenum is fully enclosed but for the air inlet and the gas-permeable plate, such that pressurized air provided through said air inlet exits the plenum through the gas-permeable deflection plate.

2. The deflection plate apparatus of claim 1, wherein said deflection plate is a metal plate made by a sintering process.

3. The deflection plate apparatus of claim 1, wherein said holder is made from a non-conductive material, and said deflection apparatus further comprises an electrode connected to said deflection plate such a charge can be applied to said deflection plate through said electrode.

4. The deflection plate apparatus of claim 1, wherein said holder is made from a conductive material.

5. A flow-type electrostatic particle sorter comprising at least one deflection plate apparatus of claim 1.

6. A flow-type electrostatic particle sorter comprising at least one deflection plate apparatus of claim 2.

7. A flow-type electrostatic particle sorter comprising at least one deflection plate apparatus of claim 3.

8. A flow-type electrostatic particle sorter comprising at least one deflection plate apparatus of claim 4.

9. The flow-type electrostatic particle sorter of claim 5, further comprising a gas supply adapted to provide pressurized gas to said plenum of said deflection plate apparatus.

10. The flow-type electrostatic particle sorter of claim 6, further comprising a gas supply adapted to provide pressurized gas to said plenum of said deflection plate apparatus.

11. The flow-type electrostatic particle sorter of claim 7, further comprising a gas supply adapted to provide pressurized gas to said plenum of said deflection plate apparatus.

12. The flow-type electrostatic particle sorter of claim 8, further comprising a gas supply adapted to provide pressurized gas to said plenum of said deflection plate apparatus.

13. A flow cytometer comprising at least one deflection plate apparatus of claim 1.

14. A flow cytometer comprising at least one deflection plate apparatus of claim 2.

15. A flow cytometer comprising at least one deflection plate apparatus of claim 3.

16. A flow cytometer comprising at least one deflection plate apparatus of claim 4.

* * * * *